(12) United States Patent
Dubuffet et al.

(10) Patent No.: US 7,166,633 B2
(45) Date of Patent: Jan. 23, 2007

(54) METHOD FOR SYNTHESISING PERINDOPRIL AND THE PHARMACEUTICALLY ACCEPTABLE SALT THEREOF

(75) Inventors: Thierry Dubuffet, Autretot (FR); Pascal Langlois, Saint Jean de la Neuville (FR)

(73) Assignee: Les Laboratories Servier, Courbevoie Cedex (FR)

( * ) Notice: Subject to any disclaimer, the term of this patent is extended or adjusted under 35 U.S.C. 154(b) by 6 days.

(21) Appl. No.: 10/547,131

(22) PCT Filed: Feb. 27, 2004

(86) PCT No.: PCT/FR2004/000446

§ 371 (c)(1),
(2), (4) Date: Aug. 24, 2005

(87) PCT Pub. No.: WO2004/078107

PCT Pub. Date: Sep. 16, 2004

(65) Prior Publication Data

US 2006/0149081 A1   Jul. 6, 2006

(30) Foreign Application Priority Data

Feb. 28, 2003   (EP) .................................. 03290485

(51) Int. Cl.
*A61K 31/403*   (2006.01)
*C07D 209/12*   (2006.01)
(52) U.S. Cl. ...................................... 514/412; 548/452
(58) Field of Classification Search ................ 548/452; 514/412
See application file for complete search history.

(56) References Cited

U.S. PATENT DOCUMENTS 4,933,361 A    6/1990   Urbach et al.

2006/0149081 A1*   7/2006   Dubuffet et al. ............ 548/492

FOREIGN PATENT DOCUMENTS

| WO | WO 0158868 | 8/2001 |
| WO | WO 03016336 | 2/2003 |

OTHER PUBLICATIONS

M Vincent, et al. "Stereoselective Synthesis of a New Perhydroindole Derivative of Chiral Iminodiacid, a Potent Inhibitor of Agiotensin Converting Enzyme", TETRAHEDRON, vol. 23, No. 16, pp. 1677-1680, 1982.
International Search Report: PCT FR2004 000446, Aug. 6, 2004.
International Preliminary Examination Report: PCT 2004 000446, Aug. 31, 2004.
International Preliminary Report on Patentability: PCT/FR2004/000446—Sep. 29, 2005.

* cited by examiner

*Primary Examiner*—Golam M. M. Shameem
*Assistant Examiner*—Michael P. Barker
(74) *Attorney, Agent, or Firm*—Hueschen and Sage

(57) ABSTRACT

Process for the synthesis of perindopril of formula (I):

and pharmaceutically acceptable salts thereof.

4 Claims, No Drawings

METHOD FOR SYNTHESISING PERINDOPRIL AND THE PHARMACEUTICALLY ACCEPTABLE SALT THEREOF

The present invention relates to a process for the synthesis of perindopril of formula (I):

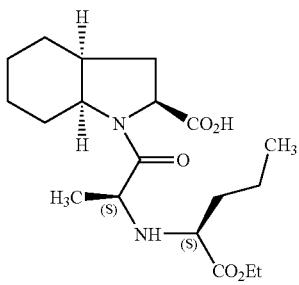

and pharmaceutically acceptable salts thereof.

Perindopril and pharmaceutically acceptable salts thereof, more especially its tert-butylamine salt, have valuable pharmacological properties.

Their principal property is that of inhibiting angiotensin I converting enzyme (or kininase II), which prevents, on the one hand, conversion of the decapeptide angiotensin I to the octapeptide angiotensin II (a vasoconstrictor) and, on the other hand, degradation of bradykinin (a vasodilator) to an inactive peptide.

Those two actions contribute to the beneficial effects of perindopril in cardiovascular diseases, more especially in arterial hypertension and heart failure.

Perindopril, its preparation and its use in therapeutics have been described in the European Patent specification EP 0 049 658.

In view of the pharmaceutical value of this compound, it has been important to obtain it by an effective synthesis process that can be readily converted to the industrial scale and that results in perindopril in a good yield and with excellent purity, starting from reasonably priced starting materials.

The patent specification EP 0 308 341 describes the industrial synthesis of perindopril by coupling (2S,3aS,7aS)-octahydroindole-2-carboxylic acid benzyl ester with N-[(S)-1-carboxybutyl]-(S)-alanine ethyl ester, followed by deprotection of the carboxylic group of the heterocycle by means of catalytic hydrogenation.

However, the (2S,3aS,7aS)-octahydroindole-2-carboxylic acid ester is not commercially available and its preparation requires several synthesis steps (including a resolution step) starting from indole-2-carboxylic acid.

The Applicant has now developed a new process for the synthesis of perindopril starting from readily accessible starting materials.

More specifically, the present invention relates to a process for the industrial synthesis of perindopril and pharmaceutically acceptable salts thereof, characterised in that 1-(1-cyclohexen-1-yl)-pyrrolidine of formula (II):

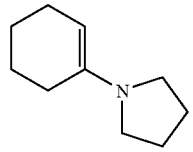

is reacted with the compound of formula (III):

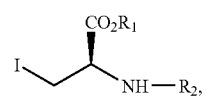

wherein $R_1$ represents a protecting group for the acid function and $R_2$ represents a protecting group for the amine function,
to yield the compound of formula (IV):

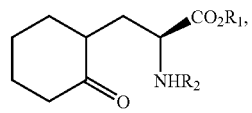

wherein $R_1$ and $R_2$ are as defined hereinbefore, the amine function of which is deprotected before cyclisation is carried out, followed by dehydration, to yield the compound of formula (V):

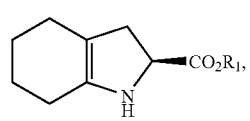

wherein $R_1$ is as defined hereinbefore,
or an addition salt thereof with a mineral or organic acid,
which is reacted with the compound of formula (VI):

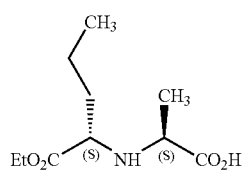

in ethyl acetate,
in the presence of an amount of 1-hydroxybenzotriazole of from 0.4 to 0.6 mol per mol of compound of formula (V) used and an amount of dicyclohexylcarbodiimide of from 1 to 1.2 mol per mol of compound of formula (V) used,
in the presence of an amount of triethylamine of from 0.25 to 1.2 mol per mol of compound of formula (V) used,
at a temperature of from 20 to 77° C.,
to yield, after isolation, the compound of formula (VII):

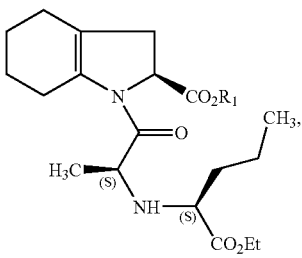

(VII)

wherein R₁ is as defined hereinbefore,
which is hydrogenated in the presence of a catalyst such as, for example, palladium, platinum, rhodium or nickel, under a hydrogen pressure of from 1 to 30 bars, preferably from 1 to 10 bars, to yield, after deprotection of the acid function, perindopril of formula (I), which is converted, if desired, into a pharmaceutically acceptable salt such as the tert-butylamine salt.

The Example hereinbelow illustrates the invention but does not limit it in any way.

EXAMPLE (2S,3aS,7aS)-1-{(2S)-2-[(1S)-1-(Ethoxycarbonyl)-butylamino]-propionyl}-octahydro-1H-indole-2-carboxylic acid tert-butylamine salt Step A: Benzyl (2S)-2-[(tert-butoxycarbonyl)-amino]-3-(2-oxocyclohexyl)-propanoate Introduce 200 g of 1-(1-cyclohexen-1-yl)-pyrrolidine, 535 g of benzyl (2S)-2-[(tert -butoxycarbonyl)-amino]-3iodopropanoate and 1.5 litres of acetonitrile into a reactor equipped with a reflux column.

Reflux for 1 hour and then return the mixture to ambient temperature. After evaporating off the solvent, add 2 litres of water and then acetic acid. Extract with ethyl acetate and evaporate to dryness. Benzyl (2S)-2-[(tert-butoxycarbonyl)-amino]-3-(2-oxocyclohexyl)-propanoate is obtained in that manner in a yield of 80%.

Step B: Benzyl (2S)-2-amino-3-(2-oxocyclohexyl)-propanoate

Introduce 200 g of the compound obtained in the previous Step, 1.5 litres of dichloromethane and 60 g of trifluoroacetic acid into a reactor. After stirring for 1 hour 30 minutes at ambient temperature, add 2 litres of saturated sodium hydrogen carbonate solution. Extract with dichloromethane and evaporate to dryness.

Benzyl (2S)-2-amino-3-(2-oxocyclohexyl)-propanoate is obtained in that manner in a yield of 90%.

Step C: Benzyl (2S)-2,3,4,5,6,7-hexahydro-1H-indole-2-carboxylate para-toluenesulphonate In a reactor, reflux 200 g of the compound obtained in the previous Step, 151.9 g of p-toluenesulphonic acid and 1 litre of toluene, the water formed being removed by azeotropic distillation. When no more water is separated off, evaporate off the toluene.

Benzyl (2S)-2,3,4,5,6,7-hexahydro-1H-indole-2-carboxylate para-toluenesulphonate is obtained in that manner in a crude yield of 97%.

Step D: Benzyl (2S)-1-{(2S)-2-[(1S)-1-(ethoxycarbonyl)-butylamino]-propionyl}-2,3,4,5,6,7hexahydro-1H-indole-2-carboxylate Introduce 200 g of the compound obtained in the previous Step, 46 g of triethylamine and 1 litre of ethyl acetate into a reactor, followed by, after stirring for 10 minutes at ambient temperature, 104 g of N-[(S)-ethoxycarbonyl-1-butyl]-(S)-alanine, 30 g of 1-hydroxybenzotriazole and 100 g of dicylohexylcarbodiimide. The heterogeneous mixture is then heated at 30° C. for 3 hours, whilst stirring well, and it is then cooled to 0° C. and filtered. The filtrate is then washed and then evaporated to dryness to yield the expected product in a yield of 95%.

Step E: (2S, 3aS, 7aS)-1-{(2S)-2-[(1S)-1-(Ethoxycarbonyl)-butylamino]-propionyl}-octahydro-1H-indole-2-carboxylic acid Introduce 200 g of the compound obtained in the previous Step, dissolved in acetic acid, and then 5 g of Pt/C 10% into a hydrogenator. Hydrogenate under a pressure of 5 bars at ambient temperature until the theoretical amount of hydrogen has been absorbed. Remove the catalyst by filtration and then cool to a temperature of from 0 to 5° C. and collect the resulting solid by filtration. Wash the filter cake and dry it to constant weight. (2S,3aS,7aS)-1-{(2S)-2-[(1S)-1-(Ethoxycarbonyl)-butylamino]-propionyl}-octahydro-1-indole-2-carboxylic acid is obtained in that manner in a yield of 85% and an enantiomeric purity of 99%.

Step F: (2S,3aS,7aS)-1-{(2S)-2-[(1S)-1-(Ethoxycarbonyl)-butylamino]-propionyl}-octahydro-1H-indole-2-carboxylic acid tert-butylamine salt The compound obtained in the previous Step (200 g) is dissolved in 2.8 litres of ethyl acetate, and then 40 g of tert-butylamine and 0.4 litre of ethyl acetate are added.

The suspension obtained is then refluxed until dissolution is complete and then the solution obtained is filtered whilst still hot and cooled to a temperature of 15–20° C., with stirring.

The precipitate obtained is then filtered, made into a paste again using ethyl acetate, dried and then comminuted to yield the expected product in a yield of 95%.

The invention claimed is:

1. A process for the synthesis of perindopril of formula (I):

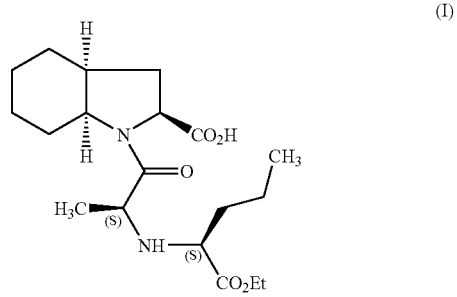

(I)

and pharmaceutically acceptable salts thereof,
wherein 1-(1-cyclohexen-1-yl)-pyrrolidine of formula (II):

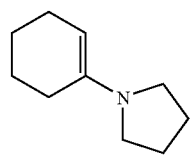

(II)

is reacted with a compound of formula (III):

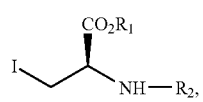

(III)

wherein $R_1$ represents a protecting group and $R_2$ represents a protecting group,
to yield the compound of formula (IV):

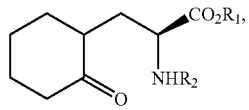

(IV)

the amine function of the compound of formula (IV) is deprotected and the deprotected intermediate thus obtained is subjected to dehydration, to yield a compound of formula (V):

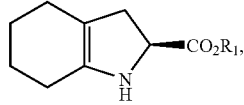

(V)

or an addition salt thereof with a mineral or organic acid,
which is reacted with the compound of formula (VI):

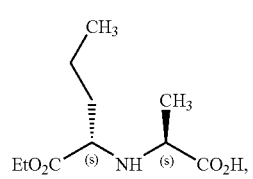

(VI)

in ethyl acetate,
in the presence of an amount of 1-hydroxybenzotriazole of from 0.4 to 0.6 mol per mol of compound of formula (V) used and an amount of dicyclohexylcarbodiimide of from 1 to 1.2 mol per mol of compound of formula (V) used,
in the presence of an amount of triethylamine of from 0.25 to 1.2 mol per mol of compound of formula (V) used,
at a temperature of from 20 to 77° C.,
to yield, after isolation, the compound of formula (VII):

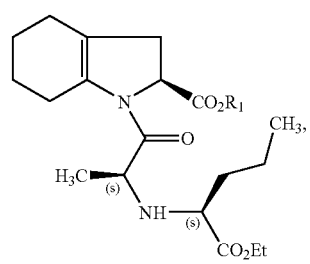

(VII)

which is hydrogenated in the presence of a catalyst, under a hydrogen pressure of from 1 to 30 bars, to yield, after deprotection of the acid function, perindopril of formula (I), which is converted, if desired, into a pharmaceutically acceptable salt.

2. The process of claim 1, wherein the hydrogen pressure during the hydrogenation reaction is from 1 to 10 bars.

3. The process of claim 1, wherein the catalyst is selected from palladium, platinum, rhodium and nickel.

4. The process of claim 1 for the synthesis of perindopril in the form of its tert-butylamine salt.

* * * * *

UNITED STATES PATENT AND TRADEMARK OFFICE
CERTIFICATE OF CORRECTION

| | |
|---|---|
| PATENT NO. | : 7,166,633 B2 |
| APPLICATION NO. | : 10/547131 |
| DATED | : January 23, 2007 |
| INVENTOR(S) | : Thierry Dubuffet et al. |

It is certified that error appears in the above-identified patent and that said Letters Patent is hereby corrected as shown below:

Cover Page, Item (73) Assignee: "Les Laboratories Servier" should be --Les Laboratoires Servier--.

Cover Page, Item (30) Priority Number: "03290485" should be --03290485.6--.

Signed and Sealed this

First Day of May, 2007

JON W. DUDAS
*Director of the United States Patent and Trademark Office*